US008816104B2

(12) United States Patent  
Wood et al.

(10) Patent No.: US 8,816,104 B2
(45) Date of Patent: Aug. 26, 2014

(54) PROCESS

(75) Inventors: Michael Anthony Wood, London (GB); Paul Willett, London (GB); Paul Appleton, London (GB)

(73) Assignee: Davy Process Technology Limited, London (GB)

( * ) Notice: Subject to any disclaimer, the term of this patent is extended or adjusted under 35 U.S.C. 154(b) by 90 days.

(21) Appl. No.: 12/919,946

(22) PCT Filed: Feb. 20, 2009

(86) PCT No.: PCT/GB2009/050171
§ 371 (c)(1),
(2), (4) Date: Dec. 9, 2010

(87) PCT Pub. No.: WO2009/106877
PCT Pub. Date: Sep. 3, 2009

(65) Prior Publication Data
US 2011/0092721 A1 Apr. 21, 2011

(30) Foreign Application Priority Data

Feb. 28, 2008 (GB) .................................. 0803663.4

(51) Int. Cl.
*C07D 307/08* (2006.01)
*B01J 23/889* (2006.01)
(52) U.S. Cl.
CPC .................................. *B01J 23/8892* (2013.01);
*C07D 307/08* (2013.01)
USPC .......................................................... 549/508
(58) Field of Classification Search
CPC .......................... B01J 23/8892; C07D 307/08
USPC .......................................................... 549/508
See application file for complete search history.

(56) References Cited

U.S. PATENT DOCUMENTS

| 4,112,245 A | 9/1978 | Zehner et al. |
| 4,584,419 A | 4/1986 | Sharif et al. |
| 4,751,334 A | 6/1988 | Turner et al. |
| 4,767,869 A | 8/1988 | Harrison et al. |
| 4,919,765 A | 4/1990 | Wilkes et al. |
| 4,945,173 A | 7/1990 | Wood |
| 4,966,970 A | 10/1990 | Lee et al. |
| 5,254,758 A | 10/1993 | Hiles et al. |
| 5,310,954 A | 5/1994 | Hiles et al. |
| 5,387,753 A | 2/1995 | Scarlett et al. |
| 6,936,727 B2 * | 8/2005 | Sutton et al. .................. 549/508 |

FOREIGN PATENT DOCUMENTS

| EP | 0301853 A1 | 2/1989 |
| EP | 1108702 A1 | 6/2001 |
| JP | H05286960 | 11/1993 |
| WO | 8603189 A1 | 6/1986 |
| WO | 8800937 A1 | 2/1988 |
| WO | 9101960 A1 | 2/1991 |
| WO | 2005058855 A | 6/2005 |
| WO | 2006037957 A | 4/2006 |

OTHER PUBLICATIONS

International Search Report for PCT/GB2009/050171, dated Aug. 26, 2009, 5 pages.
Hunter et al., "Kinetics and Mechanism of Tetrahydrofuran Synthesis via 1,4-Butanediol Dehydration in High-Temperature Water", J. Org. Chem, 2006, pp. 6229-6239, vol. 71.
Pearson, "Composite Propellent Catalysts: Copper Chromate and Chromite", Combustion and Flame, 1970, pp. 73-83.

* cited by examiner

*Primary Examiner* — Taofiq A Solola
(74) *Attorney, Agent, or Firm* — Armstrong Teasdale LLP

(57) ABSTRACT

A process for activating a reduced manganese copper catalyst comprising treating the catalyst at a temperature of more than 300° C. to about 400° C. with hydrogen.

9 Claims, No Drawings

PROCESS

The present invention relates to a process for activating a catalyst and a catalyst activated according to this process. In addition, the present invention relates to the production of ethers, optionally with the co-production of diols and/or lactones by reaction of an organic feed material in the presence of hydrogen. The reaction will generally be by hydrogenation and/or dehydration. The organic feed material is selected from dicarboxylic acids and/or anhydrides, monoesters of dicarboxylic acids and/or anhydrides, diesters of dicarboxylic acids and/or anhydrides, lactones, a mixture thereof or a mixture of two or more thereof. In particular it relates to the production of $C_4$ to $C_{12}$ ethers, optionally with the co-production of the corresponding diols and/or lactones by the reaction of di-($C_1$ to $C_4$)alkyl esters of $C_4$ to $C_{12}$ dicarboxylic acids and/or anhydrides in the presence of hydrogen. More particularly, it relates to the production of cyclic ethers.

More particularly, the present invention relates to a process for the co-production of $C_4$ compounds, more specifically tetrahydrofuran, butane-1,4-diol and/or γ-butyrolactone from a hydrocarbon feedstock comprising a dialkyl maleate by vapour phase reaction in a hydrogen rich stream. In a particularly preferred arrangement of the present invention, it relates to a process for the production of at least 20% tetrahydrofuran with co-production of butane-1,4-diol and/or γ-butyrolactone. In the most preferred arrangement it relates to the production of tetrahydrofuran with any residual butane-1,4-diol and/or γ-butyrolactone being recycled and converted to further tetrahydrofuran.

It is known to produce diols by hydrogenation of dialkyl esters of dicarboxylic acids and/or anhydrides, lactones, and mixtures thereof with a minor amount, typically no more than about 10 wt/wt % and preferably no more than 1 wt/wt %, of a monoester of the dicarboxylic acid and/or anhydride. Commercial plants have been built which produce butane-1,4-diol as the primary product with small amounts, typically up to about 10 mole %, of tetrahydrofuran and up to about 15 mole % of γ-butyrolactone by hydrogenation of a dialkyl ester of maleic acid and/or anhydride, such as dimethyl maleate or diethyl maleate, which may contain minor amounts of dialkyl fumarate and/or dialkyl succinate. Dimeth succinate or diethyl succinate have also been suggested as suitable starting materials for hydrogenation to produce butane-1,4-diol, tetrahydrofuran and γ-butyrolactone. These succinates may be formed by any suitable manner and may be from biotechnology sources.

For further information regarding the operation of these plants reference may be made, for example, to U.S. Pat. Nos. 4,584,419, 4,751,334, WO-A-86/03189, WO-A-88/00937, U.S. Pat. Nos. 4767869, 4,945,173, 4,919,765, 5,254,758, 5,310,954 and WO-A-91/01960, the disclosure of each of which is herein incorporated by reference.

Whilst many plant operators aim to maximise the yield of butane-1,4-diol and to minimise the yield of the co-products, tetrahydrofuran and γ-butyrolactone, these co-products are themselves valuable commodity chemicals. The tetrahydrofuran is normally recovered as it is an important monomer for making elastomer fibres and is also an important solvent and therefore is a commercially important chemical. The γ-butyrolactone may be recovered but, as the market for this product is small, it is often recycled to the hydrogenation step for conversion to further butane-1,4-diol and the co-product tetrahydrofuran.

The dialkyl maleates which are used as feedstock in such hydrogenation processes may be produced by any suitable means. The hydrogenation of dialkyl maleates to yield butane-1,4-diol is discussed in detail in U.S. Pat. Nos. 4,584, 419, 4,751,334 and WO-A-88/00937, which are incorporated herein by reference.

A significant portion of the butane-1,4-diol produced by conventional methods is subsequently converted to tetrahydrofuran. This conversion step has substantial cost implications both in investment and operation of the plant required for the conversion and as the importance of tetrahydrofuran increases together with its use in derivative applications, it is desirable to provide a process for the production of tetrahydrofuran without the need for this expensive downstream processing. The downstream processing of conventional methods includes recovering the butane-1,4-diol, reacting it to form the tetrahydrofuran and then refining the tetrahydrofuran product.

Typically conventional processes will produce up to approximately 10 mole % tetrahydrofuran.

It is therefore desirable to provide a process for the production of higher mole % of tetrahydrofuran without the need for expensive downstream processing.

One proposal for increasing the amount of tetrahydrofuran produced is described in WO 03/00644. In this process, the feed material is fed to a vaporisation zone where it is vaporised by and into cycle gas. The resultant stream is fed to a first reaction zone comprising catalyst where hydrogenation and dehydration occurs. An intermediate product stream is recovered and passed to a second vaporisation zone where additional feed material is added. The resultant stream is passed to a further reaction zone where hydrogenation and dehydration occurs. The process is preferably carried out in the presence of a reduced manganese promoted copper catalyst.

Whilst the above process is successful in increasing the proportion of tetrahydrofuran produced, there is a problem associated with the robustness of the catalyst to minor changes in operating conditions. In extreme cases, as conditions alter, the tetrahydrofuran making sites on the catalyst cease functioning and can be regarded as having been removed. Proposals for catalysts which are more resistant to changes in operating conditions have been suggested however, these do not generally offer the required level of conversion and/or selectivity.

A further problem with the conventional catalyst occurs where the process is operated at higher temperatures such as those that may be required to increase the tetrahydrofuran make above 90%, in that there is an increase in by-product make.

It has now been discovered that if a reduced manganese copper catalyst is activated under a hydrogen stream to temperatures of from about 300° C. to about 400° C., a catalyst which offers advantages in processes for the production of ethers is obtained.

Thus according to a first aspect of the present invention there is provided a process for activating a reduced manganese copper catalyst comprising treating the catalyst at a temperature of more than 300° C. to about 400° C. with hydrogen. In a preferred arrangement, the temperature may be from more than 300° C. to about 330° C.

By "reduced manganese" we mean that the catalyst comprises less than 0.1 wt % manganese, more preferably 0.05 wt % or less, such as 0.03 wt % manganese. The reduced manganese copper catalyst is most preferably a zero manganese copper catalyst.

It has been found that if this catalyst is used in a process for the production of an ether by reaction of a corresponding organic feed material selected from dicarboxylic acids and/or anhydrides, monoesters of dicarboxylic acids and/or anhydrides, diesters of dicarboxylic acids and/or anhydrides, lactones, and mixtures of two or more thereof in the presence of hydrogen, higher temperatures than are conventionally used, such as from about 215° C. to about 230° C. to improve ester conversion, improved selectivity to the desired ether is noted. For example, conversion of essentially 100% to the desired ether may be achieved. At these conditions, a high by-product make as indicated by butanol content, would be expected. However, surprisingly, where the catalyst has been activated in accordance with the present invention, the butanol content is lower than that obtained at similar conversions but at a 20° C. lower temperature. The activated catalyst is also found to have acceptable longevity with no degradation of ether production over time. Since the reaction can be operated at higher temperatures, the impact of any water present in the feed is also reduced.

A preferred activation process comprises the steps of:
(i) supplying a stream comprising a maximum of 0.5% hydrogen to the catalyst at room temperature;
(ii) increasing the temperature to a temperature in excess of 300° C. over a period of from 10 to 20 hours; and
(iii) increasing the hydrogen content of the stream until it is 100%.

Particular advantages are achieved wherein the stream supplied in step (i) is commenced at 0.1% hydrogen and subsequently increased stepwise to 0.5% over a period of 5 to 10 hours, more preferably about 7 hours. In a more preferred arrangement, as the hydrogen content of the stream supplied in step (i) is increased, the temperature is increased from room temperature to a temperature in the region of from about 100° C. to about 160° C.

It may be desirable to carefully monitor and adjust the hydrogen inlet and outlet content to manage the exotherm.

According to the second aspect of the present invention there is provided a catalyst activated in accordance with the above first aspect.

According to the third aspect of the present invention there is provided a process for the production of an ether by reaction of a corresponding organic feed material selected from dicarboxylic acids and/or anhydrides, monoesters of dicarboxylic acids and/or anhydrides, diesters of dicarboxylic acids and/or anhydrides, lactones, and mixtures of two or more thereof in the presence of hydrogen wherein the reaction is carried out in the presence of the catalyst of the second aspect of the present invention, or a catalyst activated in accordance with the process of the above first aspect.

In one preferred example of the third aspect of the present invention the process comprises the steps of:
(a) supplying a stream comprising the organic feed material to a first vaporisation zone and contacting said feed with cycle gas comprising hydrogen such that at least a portion of the feed material is vaporised by and into the cycle gas;
(b) supplying the cycle gas and the vaporised feed material to a first reaction zone comprising a catalyst, the reaction zone operating under reaction conditions to allow hydrogenation and dehydration to occur;
(c) recovering from the first reaction zone an intermediate product stream comprising unreacted feed material, cycle gas, desired product(s), and any co-products and byproducts;
(d) supplying the intermediate product stream to a second vaporisation zone and contacting it with additional feed material such that the said additional feed material is vaporised by and into the intermediate product stream;
(e) supplying the product of step (d) to a subsequent reaction zone comprising catalyst and operating under reaction conditions to allow hydrogenation and, if required, dehydration to occur, and
(f) recovering from the subsequent reaction zone a product stream comprising the ether,
wherein at least one of the catalyst of step (b) and (e) comprises the catalyst of the above second aspect of the present invention.

In one arrangement the catalysts used in steps (b) and (e) may be different. Where the catalysts used in step (b) and (e) are different, the catalyst used in step (b) may be an acid tolerant catalyst such as a promoted copper chromite catalyst and that for step (e) may be the catalyst of the second aspect of the present invention. A suitable catalyst for use in step (b) is the catalyst available from Davy Process Technology Ltd as PG85/1.

Whilst the preferred process above has been described with particular reference to two reaction zones, in one arrangement of the present invention, the process may include more than two reaction zones. Where there are more than two reaction zones, corresponding vaporisation zones may be located between adjacent reaction zones. Vaporisation in these subsequent zones may be made directly into the intermediate product stream from the previous reaction zone or if required a supplementary stream of cycle gas which may comprise one or more of fresh organic feed, refining recycle material and hydrogen may be included. The organic feed recycle material and/or hydrogen if present may be heated.

Where these intermediate reaction zones are present they may include the same catalysts of step (b) or (e) or, in an alternative arrangement a different catalyst may be used. In one arrangement, the catalyst may be one which is effective to hydrogenate the ester to diols and lactones such as a manganese promoted copper catalyst. A suitable manganese promoted copper catalyst is that available from Davy Process Technology Ltd as DRD 92/89A. This catalyst exhibits superior conversion of a dialkyl ester under typical operating conditions.

The catalyst used in the reaction zones may be a single catalyst or a mixture of catalysts. In a particularly preferred process the catalyst of the first reaction zone may include noble metal and/or copper-containing catalysts. Hence the catalyst of the first hydrogenation zone can be or include one or more of a palladium catalyst, a reduced copper chromite catalyst or a reduced copper containing catalyst. The same or a different catalyst may also be used in the subsequent and any additional reaction zones.

Examples of copper-containing catalysts include reduced copper oxide/zinc oxide catalysts, reduced manganese promoted copper catalysts, reduced copper chromite catalysts, and reduced promoted copper chromite catalysts.

The active catalytic species may be at least partially supported on a supporting material selected from chromia, zinc oxide, alumina, silica, silica-alumina, silicon carbide, zirconia, titania, carbon, or a mixture of two or more thereof, for example, a mixture of chromia and carbon.

In one arrangement, a bed comprising a variety of catalysts may be used provided that at least one catalyst in one bed is the catalyst of the above second aspect of the present invention. In one example, the bed may include a catalyst that is tolerant of residual feed acid content, one which is suitable to promote hydrogenation of the ester and the promoted copper catalyst which does not include manganese is used which promotes selectivity to the desired ether. Catalyst beds comprising more than one type of catalyst may comprise discrete layers of catalyst within the bed such that different types are separated or the different catalyst types may be admixed.

In cases where the ester feed contains acidic components, a guard bed of a suitable catalyst may be present to hydrogenate the acid and protect the catalyst of the second aspect of the present invention.

In the ether production reaction of the present invention, the conversion of the acid, anhydride and/or the lactone or ester to form the diol is an ester hydrogenation or hydrogenolysis and the reaction of the diol to the ether, is a dehydration reaction.

Without wishing to be bound by any theory, it is believed that the preferred process allows that the amount of product produced as light boiling (higher vapour pressure) ether rather than diol is increased, such that the outlet dewpoint of the reactor moves below the operating temperature such that further feed material can be vaporised into the stream until the stream approaches saturation. This is in contrast to conventional processes for the production of diols which the inlet and outlet of the reactor are close to the vapour dewpoint. The additional feed material vaporised by the process of the present invention may then be converted to product in the second reaction zone.

The cycle gas will normally contain a high concentration of hydrogen gas but may also include other gases including hydrocarbons, carbon oxides, methane, nitrogen. Further, where the cycle gas includes recycled gases from downstream, condensables including product ether, $C_1$ to $C_4$ alkanol, water, co-products and by-products may also be present.

In a particularly preferred aspect of the third embodiment of the present invention the ether is a cyclic ether. Most preferably the cyclic ether is tetrahydrofuran. In this latter case the organic feed material is preferably dialkyl maleate. Co-products which may be present to a greater or lesser extent in this embodiment or which may be absent include butane-1,4-diol and γ-butyrolactone. This reaction is illustrated in Scheme 1. In this example the alkanol is methanol and the intermediate material is partially hydrogenated dimethyl succinate.

By-products may include the alkanol used in the esterification of the acid or anhydride, for example methanol, undesirable material formed in side reactions, for example butanol, water evolved in the dehydration of the diol to the ether and intermediate material, for example dimethyl succinate together with other light or heavy materials formed in the process.

Scheme 1

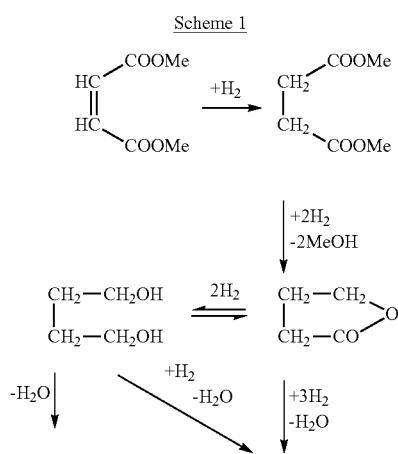

-continued

The by-products may be separated from the ether in a refining zone and may be further purified if required. Similarly, the co-products may be separated from the ether in the refining zone and may be further purified if required.

However, in one arrangement, one or more of the co-products and/or by-products will be recycled to the vaporisation zone where they will be vaporised. In one alternative arrangement, one or more of the co-products and/or by-products will be recycled to the second vaporisation zone where they will be vaporised into the intermediate product stream exiting from the first reaction zone.

Thus, in the preferred embodiment any dialkyl succinate present as a by-product may be recycled to the first vaporisation zone and hence to the first reaction zone to improve the overall selectivity of the reaction to the desired tetrahydrofuran and co-products butane-1,4-diol and/or γ-butyrolactone.

Cycle gas recovered from the subsequent reaction zone will preferably be compressed, recycled and mixed with make-up hydrogen prior to being heated and recycled to the vaporisation zone.

Any aqueous alkanol stream separated from the product may be recycled to an upstream esterification zone.

The feed material to the, or each, vaporisation zone may be, or may include, one or more recycle streams. Fresh organic feed and refining recycle streams may be vaporised together or may be vaporised in separate parts of the or each vaporisation zone. This is particularly advantageous as it will minimise the risk of transesterification between the ester and the diol.

In one arrangement, all of the cycle gas and the organic feed fed to the first vaporisation zone (step a) is supplied to the first reaction zone (step b) with the remaining organic feed and refining recycles being vaporised (step d) into the intermediate product stream recovered from the first reaction zone (step c) to form the intermediate feed stream which is fed to the subsequent reaction zone (step d).

In a second alternative arrangement, the gaseous stream from the first vaporiser (step a) may be divided with a major portion, preferably from about 70% to about 80%, being supplied to the first reaction zone (step b) and a minor portion, preferably from about 20% to about 30%, by-passing the first reaction zone and being fed to the subsequent vaporisation zone, preferably one part of the subsequent vaporisation zone (step d), where it is further heated such that additional organic feed material can be vaporised into the cycle gas before yielding a hot secondary feed stream. Where the minor portion is fed to one part of the subsequent vaporisation zone, the intermediate product stream recovered from the first reaction zone (step c) is fed to a second part of the subsequent vaporisation zone (step d) into which the refining recycles are fed. The two streams from the two separate parts of the subsequent vaporisation zone are then mixed to yield the intermediate feed stream which is fed to the subsequent reaction zone (step e).

One advantage of this preferred embodiment is that the liquid additional organic feed, which may be or include an ester, is separate from the liquid refining recycles which contain diols and/or lactones, and is only mixed therewith in the vapour phase. This will minimise the contact time and hence the potential for transesterification and progressive chain length growth.

The feed material fed to the or each vaporisation zone may be wholly, or may include, one or more recycle streams.

The cycle gas will normally contain a high concentration of hydrogen gas but may also include other gases including hydrocarbons, carbon oxides, methane, nitrogen. Further, where the cycle gas includes recycled gases from downstream, condensables including product ether, $C_1$ to $C_4$ alkanol, water, co-products and by-products may also be present.

The feed material to the vaporisation zone may be, or may include, one or more recycle streams. Fresh organic feed and refining recycle streams may be vaporised together or may be vaporised in separate parts of the vaporisation zone. This is particularly advantageous as it will minimise the risk of transesterification between the ester and the diol.

The organic feed material is preferably selected from mono $C_1$ to $C_4$ alkyl esters of $C_4$ to $C_{12}$ dicarboxylic acids and/or anhydrides, di $C_1$ to $C_4$ alkyl esters of $C_4$ to $C_{12}$ dicarboxylic acids and/or anhydrides, lactones of $C_4$ to $C_{12}$ hydroxycarboxylicacids, and mixtures of two or more thereof.

For example, the organic feed material can be selected from mono-($C_1$ to $C_4$ alkyl) esters of $C_4$ dicarboxylic acids and/or anhydrides, di-($C_1$ to $C_4$) alkyl esters of $C_4$ dicarboxylic acids and/or anhydrides, γ-butyrolactone, and mixtures of two or more thereof. A particularly preferred organic feed material may be selected from monomethyl maleate, monomethyl fumarate, monomethyl succinate, dimethyl maleate, dimethyl fumarate, dimethyl succinate, γ-butyrolactone, recycle γ-butyrolactone and/or butane-1,4-diol and mixtures of two or more thereof. Alternatively the organic feed material can be selected from monoethyl maleate, monoethyl fumarate, monoethyl succinate, diethyl maleate, diethyl fumarate, diethyl succinate, γ-butyrolactone, recycle γ-butyrolactone and/or butane-1,4-diol and mixtures of two or more thereof.

In one arrangement, the organic feed material fed to the vaporisation zone is contained within an organic solvent. Where the organic solvent is present, the vaporisation zones is operated such that the organic feed material is essentially separated from the organic solvent by cycle gas stripping.

Suitable organic solvents include: di-($C_1$ to $C_4$ alkyl) esters of alkyl dicarboxylic acids containing up to 13 carbon atoms; mono- and di-($C_{10}$ to $C_{18}$ alkyl)esters of maleic acid, fumaric acid, succinic acid and mixtures thereof; ($C_1$ to $C_4$ alkyl) esters of napthalenemonocarboxylic acids; tri-($C_1$ to $C_4$ alkyl)esters of aromatic tricarboxylic acids; di-($C_1$ to $C_4$ alkyl) esters of isophthalic acid; alkyl phthalates; and dimethyl sebecate.

The stream to the first reaction zone preferably has a hydrogen-containing cycle gas:vaporised feed ratio in the range of from about 50:1 to about 1000:1. Typically the stream to the first reaction zone will be at a temperature of from about 100° C. to about 300° C., more preferably from about 150° C. to about 250° C. Any suitable pressure may be used but the feed pressure to the first reaction zone is typically from about 50 psia (about 344.74 kPa) to about 2000 psia (about 13789 kPa). In one arrangement, pressures in the region of from about 450 psia (about 3102.64 kPa) to 1000 psia (about 6894.76 kPa). The feed to the first reaction zone is preferably supplied to the first reaction zone at a rate corresponding to a liquid hourly space velocity of from about $0.05\ h^{-1}$ to about $5.0\ h^{-1}$.

If desired, the pressure and/or the temperature can be adjusted in any convenient manner between the reaction zones. The temperature may be adjusted by any suitable means including the use of a heat exchanger or exchangers.

The hydrogen make-up gas used in the process of the present invention can be obtained by any conventional manner. Preferably it contains at least about 50 volume % up to about 99.99 volume % or more, e.g. from about 80 to about 99.9 volume %, of hydrogen. It may further contain one or more inert gases, such as nitrogen or methane. Conveniently the hydrogen make-up gas is produced by pressure swing absorption so that the cycle gas molecular weight is minimised thereby reducing the power required for compression and circulation of the cycle gas.

Typically the hydrogenatable material will contain from about 0.01 to about 1.0 wt/wt % or more, e.g. up to about 10 wt/wt %, but normally no more than about 2.0 wt/wt %, of acidic material.

The charge of catalyst in the first reaction zone is preferably sufficiently large to reduce the content of acidic material to less than about 0.005 wt/wt % in passage of the vaporous mixture therethrough.

The amount of catalyst used in each reaction zone may be the same or different. The catalyst charge in the first reaction zone may constitute from about 10% to about 70%, more usually about 20% to about 50%, of the total catalyst volume in the reaction zones. Similarly the catalyst of the subsequent reaction zone is typically in the range of from about 70% to about 10%, more usually about 20% to about 50%, of the total catalyst volume of the reaction zones.

The selected catalyst preferably converts the ester, preferably the dialkyl maleate, to the desired ether, preferably a cyclic ether most preferably tetrahydrofuran, at a selectivity of from about 20% to about 90% or more, most preferably, about 70% or more. Selectivity approaching 100% is particularly desirable.

The product stream from the final reaction zone is preferably fed, preferably having been condensed, to a refining zone where the desired ether, preferably tetrahydrofuran, is separated as product. Any co-products, such as butane-1,4-diol and/or γ-butyrolactone, which may be present may be separated or may be recycled to the reaction system. Where there is more than one co-product, one or more may be separated and recovered and the remainder recycled.

In one arrangement where 100% conversion to ether, for example tetrahydrofuran, is desired all of the co-products, for example butane-1,4-diol and/or γ-butyrolactone, are recycled.

Any alkanol derived from the organic feed, which will typically be a $C_1$ to $C_4$ alkanol and water in the crude product stream will preferably be condensed and separated in refining The alkanol will conventionally be recycled to the esterification reactor in which the organic feed material is formed, if present. The refining system may include means, if required to separate the water from the alkanol. The refining system will usually include means to separate other by-products which may be recycled. An example of a by-product which may be recycled is an for example any intermediate material. Alternatively some or all of any by-products produced may be rejected as effluent. An example of a by-product which may be recycled is any mono-ol produced.

Where wetting of the catalyst may cause the catalyst to deteriorate it may be desirable to feed the reaction mixture to the reactor above the dew point. This can be achieved by either passing a suitable excess cycle gas flow through the vaporiser or adding extra cycle gas flow after the vaporiser, or adding extra heat to the reaction mixture before feeding to the reaction zone. However, if wetting of the catalyst is not deleterious to the operation of the catalyst, entrained liquid may be present. The reaction will, however, still be essentially a vapour phase reaction.

Further details of a suitable process can be found in WO03/00644 which is incorporated herein by reference.

The invention will now be further described with reference to the accompanying examples.

EXAMPLE 1

In order to activate the copper catalyst DRD 92/89 "D" catalyst available from Davy Process Technology Limited, 500 mls were placed in the reaction zone. The gas rate was established at 1250 NLPH. The pressure was set at 50 psig. The following procedure was then followed:

1. Hydrogen concentration was increased to 0.1% whilst at room temperature. The inlet temperature was then increased to 120° C. over 3 hours. The hydrogen inlet/exit composition was monitored once temperatures in excess of 100° C. and the hydrogen inlet was maintained at 0.1%.

In steps 2 to 6, the exotherm was prevented from exceeding 10° C. by reducing the hydrogen inlet composition if required and held at the conditions until the exotherm was reduced.

2. The temperature was increased by 10° C. until it reached 160° C.
3. After holding at 160° C. for 1 hour, the inlet gas hydrogen composition was increased to 0.2% over 1 hour and held at those conditions for 2 hours.
4. The hydrogen content of the inlet composition was increased to 0.3% and held for 2 hours.
5. The hydrogen content of the inlet composition was increased to 0.4% and held for 2 hours.
6. The hydrogen content of the inlet composition was increased to 0.5% and until the hydrogen content of the inlet equalled that of the hydrogen exit.
7. The hydrogen inlet composition of 0.5% was maintained and the temperature was increased to 340° C. over 12 hours. It was ensured that the exotherm did not exceed 10° C. and held until the hydrogen inlet equalled the hydrogen exit.
8. The temperature was held at 340° C. for 1 hour.
9. The hydrogen inlet was increased to 1% over a period of 1 hour and maintained until the hydrogen inlet equalled the hydrogen exit. The exotherm was kept below 10° C. by reducing hydrogen concentration if required.
10. The hydrogen concentration at the inlet was then increased up to 5% over four hours.
11. The hydrogen content at the inlet was then increased to 10% and this was maintained until the hydrogen inlet equalled the hydrogen exit. The exotherm was kept below 10° C.
12. The hydrogen concentration was then increased to 100% ensuring that the exotherm did not exceed 10%.
13. The pressure was increased to the operating pressure of the reaction. The catalyst was then cooled to the required temperature and allowed to rest under hydrogen for 4 hours before providing feed.

EXAMPLES 2 TO 5

Catalyst DRD 92/89 D obtained from Davy Process Technology Ltd and activated as detailed above was used in a process for the production of tetrahydrofuran from a feed comprising maleic anhydride. The reaction conditions are detailed in Table 1 and the results in Table 2.

TABLE 1

| | Example 2 | Example 3 | Example 4 | Example 5 |
|---|---|---|---|---|
| Inlet Temperature ° C. | 194 | 194 | 204 | 217 |
| Exit Temperature ° C. | 190 | 189 | 198 | 210 |
| Pressure psig | 885 | 900 | 900 | 900 |
| Hydrogen:ester | 352 | 246 | 246 | 246 |
| True LHSV, hr$^{-1}$ | 0.344 | 0.344 | 0.344 | 0.344 |

TABLE 2

| Selectivities, mole % | Example 2 | Example 3 | Example 4 | Example 5 |
|---|---|---|---|---|
| Tetrahydrofuran | 83.21 | 82.69 | 92.78 | 97.43 |
| n-butanol | 0.15 | 0.15 | 0.25 | 0.52 |
| γ-butyrolactone | 11.79 | 13.38 | 4.07 | 0.13 |
| 1,4-butanediol | 1.63 | 1.85 | 0.70 | 0.00 |
| Conversion, mole % | 67.72 | 67.48 | 91.59 | 99.28 |

EXAMPLE 6

Catalyst DRD 92/89 D obtained from Davy Process Technology Ltd was activated as described above and was used in combination with catalyst DRD 92/89 A from Davy Process Technology. The combined catalyst was used in a process for the production of tetrahydrofuran from a feed comprising maleic anhydride. The reaction conditions are detailed in Table 3 and the results in Table 4.

COMPARATIVE EXAMPLE 7

Catalyst DRD 92/89 D obtained from Davy Process Technology Ltd was activated according to conventional methods and was used in combination with catalyst DRD 92/89 A from Davy Process Technology. The combined catalyst was used in a process for the production of tetrahydrofuran from a feed comprising maleic anhydride. The reaction conditions are detailed in Table 3 and the results in Table 4.

Despite the fact that twice as much of the Type D catalyst is used in Comparative Example 7 than is used in Example 6, the selectivity to the tetrahydrofuran is substantially improved where the catalyst has been subjected to the activation process of the present invention.

TABLE 3

| | Example 6 | Comparative Example 7 |
|---|---|---|
| Catalyst | 65 wt % DRD 92/89A<br>35 wt % DRD 92/89D | 30 wt % DRD 92/89A<br>70 wt % DRD 92/89D |
| Inlet Temperature ° C. | 186 | 182 |
| Exit Temperature ° C. | 198 | 200 |
| Pressure psig | 885 | 885 |
| Hydrogen:ester | 350 | 346 |
| True LHSV, hr$^{-1}$ | 0.344 | 0.344 |

TABLE 4

| Selectivities, mole % | Example 6 | Comparative Example 7 |
|---|---|---|
| Tetrahydrofuran | 89.98 | 48.10 |
| n-butanol | 4.29 | 2.25 |
| γ-butyrolactone | 0.71 | 7.67 |
| 1,4-butanediol | 4.55 | 41.59 |
| Conversion, mole % | 99.95 | 99.85 |

EXAMPLE 8

Catalyst DRD 92/89 D obtained from Davy Process Technology Ltd was activated as described above and was used in a process for the production of tetrahydrofuran from a feed comprising maleic anhydride. The reaction conditions are detailed in Table 5 and the results in Table 6

COMPARATIVE EXAMPLES 9 AND 10

Catalyst DRD 92/89 D obtained from Davy Process Technology Ltd was activated according to conventional low temperature processes. The catalyst was used in a process for the production of tetrahydrofuran from a feed comprising maleic anhydride. The reaction conditions are detailed in Table 5 and the results in Table 6

TABLE 5

|  | Example 8 | Comparative Example 9 | Comparative Example 10 |
| --- | --- | --- | --- |
| Temperature ° C. | 190 | 180 | 197 |
| Pressure, psig | 900 | 900 | 900 |
| LHSV, $hr^{-1}$ | 0.34 | 0.33 | 0.33 |
| Hydrogen:Ester | 350 | 377 | 378 |
| Residence Time, s | 6.61 | 6.8 | 6.6 |

TABLE 6

| Selectivities, mol % | Example 8 | Comparative Example 9 | Comparative Example 10 |
| --- | --- | --- | --- |
| Tetrahydrofuran | 83.21 | 45.1 | 69.8 |
| 1,4-butanediol | 0.15 | 29.1 | 19.2 |
| γ-butyrolactone | 11.79 | 21.2 | 7.2 |
| Conversion % | 67.7 | 50.6 | 60.1 |

The invention claimed is:

1. A process for the production of an ether by reaction of a corresponding organic feed material selected from dicarboxylic acids and/or anhydrides, monoesters of dicarboxylic acids and/or anhydrides, diesters of dicarboxylic acids and/or anhydrides, lactones, and mixtures of two or more thereof in the presence of hydrogen wherein the reaction is carried out in the presence of an activated catalyst, the process further comprising producing the activated catalyst by a process comprising treating a reduced catalyst at a temperature of more than 300° C. to about 400° C. with hydrogen comprising the steps of:
   (i) supplying a stream comprising a maximum of 0.5% hydrogen to the reduced catalyst at room temperature;
   (ii) increasing the temperature to a temperature in excess of 300° C. over a period of from 10 to 20 hours; and
   (iii) increasing the hydrogen content of the stream until it is 100%;
   wherein the stream supplied in step (i) is commenced at 0.1% hydrogen and subsequently increased stepwise to 0.5% over a period of 5 to 10 hours, and
   wherein as the hydrogen content of the stream supplied in step (i) is increased, the temperature is increased from room temperature to a temperature in the region of from about 100° C. to about 160° C.

2. A process according to claim 1 comprising the steps of:
   (a) supplying a stream comprising the organic feed material to a first vaporisation zone and contacting said feed with cycle gas comprising hydrogen such that at least a portion of the feed material is vaporised by and into the cycle gas;
   (b) supplying the cycle gas and the vaporised feed material to a first reaction zone comprising a catalyst, the reaction zone operating under reaction conditions to allow hydrogenation and dehydration to occur;
   (c) recovering from the first reaction zone an intermediate product stream comprising unreacted feed material, cycle gas, desired product(s), and any co-products and by-products;
   (d) supplying the intermediate product stream to a second vaporisation zone and contacting it with additional feed material such that the said additional feed material is vaporised by and into the intermediate product stream;
   (e) supplying the product of step (d) to a subsequent reaction zone comprising catalyst and operating under reaction conditions to allow hydrogenation and, if required, dehydration to occur, and
   (f) recovering from the subsequent reaction zone a product stream comprising the ether,
   wherein at least one of the catalyst of step (b) and (e) comprises the catalyst of claim 1.

3. A process according to claim 2 wherein the catalyst used in step (b) comprises a promoted copper chromite catalyst.

4. A process according to claim 2 wherein the process further comprises one or more additional subsequent reaction zones located in series between the first and final subsequent reaction zone and wherein the or each additional subsequent reaction zone is preceded by a vaporisation zone in which additional feed, recycle or fresh feed and recycle are vaporised by and into the intermediate product stream from the previous reaction zone.

5. A process according to claim 4 wherein the catalyst in the intermediate reaction zone is a manganese promoted copper catalyst.

6. A process according to claim 2 wherein the feed material is selected from mono $C_1$ to $C_4$ alkyl esters of $C_4$ to $C_{12}$ dicarboxylic acids and/or anhydrides, di $C_1$ to $C_4$ alkyl esters of $C_4$ to $C_{12}$ dicarboxylic acids and/or anhydrides, lactones of $C_4$ to $C_{12}$ hydroxycarboxylic acids, and mixtures of two or more thereof.

7. A process according to claim 6 wherein the feed material is selected from monomethyl maleate, monomethyl fumarate, monomethyl succinate, dimethyl maleate, dimethyl fumarate, dimethyl succinate, Y-butyrolactone, recycle Y-butyrolactone and/or butane-1,4-diol and mixtures of two or more thereof.

8. A process according to claim 2 wherein the ether is a cyclic ether.

9. A process according to claim 8 wherein the ether is tetrahydrofuran.

* * * * *